United States Patent [19]

Blank et al.

[11] Patent Number: 4,868,347
[45] Date of Patent: Sep. 19, 1989

[54] PROCESS FOR OBTAINING SUBSTITUTED FLUOROBENZENES

[75] Inventors: Heinz U. Blank, Odenthal; Edwin Ritzer, Burscheid, both of Fed. Rep. of Germany

[73] Assignee: Bayer Aktiengesellschaft, Leverkusen, Fed. Rep. of Germany

[21] Appl. No.: 130,700

[22] Filed: Dec. 9, 1987

[30] Foreign Application Priority Data

Dec. 11, 1986 [DE] Fed. Rep. of Germany ....... 3642326

[51] Int. Cl.$^4$ .............................................. C07C 79/12
[52] U.S. Cl. ................................... 568/937; 568/938; 558/411; 558/425; 562/438; 562/405; 562/458
[58] Field of Search ............... 558/411, 425; 562/438, 562/439, 458, 405; 570/127

[56] References Cited

U.S. PATENT DOCUMENTS

| | | |
|---|---|---|
| 3,140,319 | 7/1964 | Sparks .................................. 568/937 |
| 3,183,275 | 5/1965 | Sparks .................................. 568/937 |
| 3,423,475 | 1/1969 | Weinstock ........................... 568/937 |
| 3,949,008 | 4/1976 | Rosenblatt et al. ................. 568/937 |
| 3,993,704 | 11/1976 | Marsh et al. ........................ 568/937 |
| 4,226,811 | 10/1980 | Oeser et al. ......................... 568/937 |
| 4,339,618 | 7/1982 | Rosner ................................ 568/937 |
| 4,593,144 | 6/1986 | Chupp et al. ................... 568/937 X |
| 4,642,398 | 2/1987 | Cantrell .............................. 568/937 |

Primary Examiner—John F. Terapane
Assistant Examiner—Susan Wolffe
Attorney, Agent, or Firm—Sprung Horn Kramer & Woods

[57] ABSTRACT

Substituted fluorobenzenes which are produced in aprotic, polar solvents or in mixtures which contain such solvents can be obtained by extracting the substituted fluorobenzenes from the solvents or solvent mixtures with aliphatic extracting agents and then seaprating the extracting agents from the substituted fluorobenzenes.

16 Claims, No Drawings

PROCESS FOR OBTAINING SUBSTITUTED FLUOROBENZENES

The present application relates to a process for obtaining substituted fluorobenzenes from aprotic, polar solvents or mixtures containing such solvents, which is characterized in that the substituted fluorobenzenes are extracted from the solvents/solvent mixtures with aliphatic extracting agents, and the extracting agents are then separated from the substituted fluorobenzenes, or the substituted fluorobenzenes are subjected to a chemical reaction in the extracting agents and the extracting agents are separated from the reaction products of the substituted fluorobenzenes.

In the preparation of substituted fluorobenzenes, the latter are frequently produced in aprotic, polar solvents or in mixtures which contain aprotic, polar solvents. Examples of preparation processes which lead to such solutions are nucleophilic substitution reactions, such as the preparation of 3,5-dichloro-2,4-difluoronitrobenzene from 2,3,4,5-tetrachloro-nitrobenzene and potassium fluoride in dimethylsulfoxide (DMSO), described in U.S. Pat. No. 3,294,629.

The isolation of strongly polar substituted fluorobenzenes from the likewise strongly polar aprotic solvents comes up against considerable difficulties due to the high reactivity and thermal sensitivity of the substances to be isolated as a consequence of their frequently manifold substitution, and furthermore difficulties due to the always high boiling points of the suitable aprotic, polar solvents.

Thus, it is possible to obtain substituted fluorobenzenes directly by distillation without overlong thermal load only when the substituted fluorobenzene has a lower boiling point than the solvent used during its preparation. If the solvent has a lower boiling point than the substituted fluorobenzene, the solvent must first be removed by distillation with thermal load of the desired product. In general, various washing and purification processes are then required for the further work-up of the distillation residue containing the desired product (EP No. 52,833). In the case where the boiling points of the substituted fluorobenzene and the solvent are identical or very similar or in the case where azeotropes form, direct distillation is not possible to a satisfactory extent, even with very complex equipment.

In order to avoid the decomposition and side reactions to be feared at high distillation temperatures, the reaction mixture present in an aprotic, polar solvent after the nucleophilic substitution has in many cases, including in the abovementioned U.S. Pat. No. 3,294,629, been mixed with an excess amount of water, relative to the amount of this solvent. In this procedure, the substituted fluorobenzene precipitates and deposits as a solid or as an oily phase. For further work-up and purification, the deposited substituted fluorobenzene is taken up in a polar solvent.

The advantage of polar, aprotic solvents in nucleophilic substitution reactions on aromatics has long been known, since, for example, the reaction can hereby be carried out at lower temperatures than when a solvent is not used. Since these solvents must be aprotic, they must also contain no water. In order to recover the polar, aprotic solvents, the water/solvent mixture must therefore be worked up by distillation after aqueous work-up, as described above. Since the water generally has a lower boiling point than the polar, aprotic solvents, it must first be removed by distillation, and the solvent can only be obtained subsequently. Particularly for this reason, this distillation is very energy-consuming because the water is present in a large excess, since, in the aqueous work-up described above, the most complete precipitation possible of the substituted fluorobenzene to be obtained is to take place and, furthermore, phase separation between the oily substituted fluorobenzene and the water/solvent mixture is poor if inadequate water is added. Subsequent to the distillative removal of water and solvent, an absolutization process, more or less expensive to carry out, for the solvent follows before it is reused. Similar difficulties with respect to the recovery of the solvent also arise in the attempt to obtain substituted fluorobenzene from the solvent by steam distillation (U.S. Pat. No. 4,140,719).

It is known (German Auslegeschrift No. 1,269,272; Erdöl und Kohle-Erdgas-Petrochemie 21 (1968), 275) that benzene, toluene and xylene can be obtained from hydrocarbons by extraction using dimethyl sulphoxide (DMSO), N-methyl-pyrrolidone (NMP), ethylene glycol and other polar extracting media. In this case, the extracting agent is the stronger polar substance compared to the remaining hydrocarbon mixture which is to be regarded as solvent. In this case, the addition of a small amount of water to the extracting agent has been proposed, whereby the selectivity of the latter can be increased, but, at the same time, the capacity for the aromatics mentioned drops. In the case of the simple and less polar aromatics benzene, toluene and xylene, recovery from the mixture with DMSO by extraction with paraffins is also possible if amounts of water of up to 15% are added to the DMSO (Erdöl und Kohle-Erdgas-Petrochemie, loc. cit.; Hydrocarbon Processing 47 (September 1968), 177 and 51 (September 1972), 185).

In view of these correlations, it is surprising that highly polar, substituted fluorobenzenes can be extracted from polar aprotic solvents using virtually non-polar aliphatic extracting agents. This extraction is even possible when no water has been added to these aprotic, polar solvents.

Substituted fluorobenzenes which can be obtained in the process according to the invention are those of the general formula

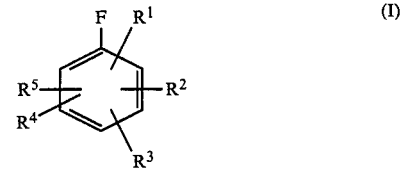

in which
R$^1$ represents an NO$_2$, CN, COF or CF$_3$ group which is in the ortho- or para-position to fluorine and, in the case where at least three of the radicals R$^2$ to R$^5$ represent chlorine or bromine, of which one is in the ortho-position to the fluorine, the second may also be chlorine or bromine in the ortho-position,
R$^2$ denotes hydrogen, halogen or an NO$_2$, CN, COF, CF$_3$, COOR$^6$, COR$^7$, SO$_2$R$^7$, SO$_2$—N(R$^6$)$_2$ or CO—N(R$^6$)$_2$ group, in which
R$^6$ denotes alkyl or phenyl, and
R$^7$ denotes alkyl, phenyl or substituted phenyl, $R^3$ denotes hydrogen, halogen, alkyl or an $NO_2$ group, and $R^4$ and $R^5$, independently of one another, denote hydrogen or halogen.

Halogen is, for example, fluorine, chlorine or bromine, preferably fluorine or chlorine.

Alkyl has, for example, 1-6, preferably 1-4, particularly preferably 1-2, C atoms, such as methyl, ethyl, propyl, isopropyl, butyl, isobutyl, amyl and hexyl. Methyl is very particularly preferred.

In the case of a substituted phenyl, one or more of the substituents which are mentioned under $R^1$ and $R^2$ are suitable. They may be identical or different.

Substances covered by formula I) are, for example: nitrofluorobenzenes, such as, for example 2-fluoronitrobenzene, 4-fluoronitrobenzene, 4-fluoronitrobenzene, 2,4-difluoronitrobenzene, 2,6-difluoronitrobenzene and 2,4,6-trifluoronitrobenzene; nitrochlorofluorobenzenes, such as, for example, 3-chloro-4-fluoronitrobenzene, 3-chloro-2-fluoronitrobenzene, 5-chloro-2-fluoronitrobenzene, 3-chloro-2,4-difluoronitrobenzene, 5-chloro-2,4-difluoronitrobenzene, 3-3,5-dichloro-2-fluoronitrobenzene, 3,5-di-chloro-4-fluoronitrobenzene and 3,5-dichloro-2,4-difluoronitrobenzene; nitrofluorotoluenes, such as, for example, 2-fluoro-5-nitrotoluene, 3-fluoro-6-nitrotoluene, 2-fluoro-3-nitrotoluene, 3-fluoro-4-nitrotoluene, 4-fluoro-3-nitrotoluene and 3-fluoro-2-nitrotoluene; dinitrofluorobenzenes, such as, for example, 2,4-dinitrofluorobenzene, 2,6-dinitrofluorobenzene, 2,3-dinitrofluorobenzene, 3,4-dinitro-fluorobenzene and 2,5-dinitrofluorobenzene; dinitrochlorofluorobenzenes, such as, for example, 6-chloro-2,4-dinitro-fluorobenzene and 4-chloro2,6-dinitro-fluorobenzene; fluorobenzonitriles, such as, for example, 4-fluorobenzonitrile, 2-fluorobenzonitrile, 2,4-difluorobenzonitrile, 2,6-difluorobenzonitrile, 3,5-difluorobenzonitrile, 3,4-difluorobenzonitrile, 2,3-difluorobenzonitrile, 2,4,6-trifluorobenzonitrile, 2,3,4-trifluorobenzonitrile, 2,4,6-trifluorobenzonitrile, 2,3,5-trifluorobenzonitrile, 3,4,5-trifluorobenzonitrile, 2,3,6-trifluorobenzonitrile, 2,3,4,5-tetrafluorobenzonitrile, 2,3,4,6-tetrafluorobenzonitrile, 2,3,5,6-tetrafluorobenzonitrile and pentafluorobenzonitrile; fluorobenzoyl fluorides, such as, for example, 4-fluorobenzoyl fluoride, 2-fluorobenzoyl fluoride, 2,4-difluorobenzoyl fluoride, 2,6-difluorobenzoyl fluoride, 3,5-difluorobenzoyl fluoride, 3,4-difluorobenzoyl fluoride, 2,3-difluorobenzoyl fluoride, 2,4,6-trifluorobenzoyl fluoride, 2,3,4-trifluorobenzoyl fluoride, 2,4,6-trifluorobenzoyl fluoride, 2,3,5-trifluorobenzoyl fluoride, 3,4,5-trifluorobenzoyl fluoride, 2,3,6-trifluorobenzoyl fluoride, 2,3,4,5-tetrafluorobenzoyl fluoride, 2,3,4,6-tetrafluorobenzoyl fluoride, 2,3,5,6-tetrafluorobenzoyl fluoride and pentafluorobenzoyl fluoride; fluoro-trifluoromethylbenzenes, such as, for example, 4-fluoro-trifluoromethylbenzene, 2-fluoro-trifluoromethyl-benzene, 2,4-difluoro -trifluoromethyl-benzene, 2,6-difluoro-trifluoromethylbenzene, 3,5-difluoro-trifluoromethyl-benzene, 3,4-difluoro-trifluoromethyl-benzene, 2,3-difluoro-trifluoromethyl -benzene, 2,4,6-trifluoro-trifluoromethyl-benzene, 2,3,5-trifluoro-trifluoromethyl-benzene, 2,4,5-trifluoro -trifluoromethyl-benzene, 2,3,6-trifluoro-trifluromethyl fluoromethyl-benzene, 2,3,4,5-tetrafluoro-trifluoro- methyl-benzene, 2,3,4,6-tetrafluoro-trifluoromethylbenzene, 2,3,5,6-tetrafluoro-trifluoromethyl-benzene and pentafluoro-trifluoromethyl-benzene; chlorofluoro-benzonitriles, such as, for example, 3-chloro-4-fluorobenzonitrile, 3-chloro-2-fluorobenzonitrile, 3-chloro-6-fluorobenzonitrile, 3,5-dichloro-4-fluorobenzonitrile, 3,5-dichloro-2-fluorobenzonitrile, 3-chloro-2,6-difluorobenzonitrile, 3-chloro-2,4-difluorobenzonitrile, 5-chloro-2,4-difluorobenzonitrile, 5-chloro-3,4-difluorobenzonitrile, 3,5-dichloro-2,4-difluorobenzonitrile, 3,5-dichloro-2,6-difluorobenzonitrile and 3,5-dichloro-2,4,6-trifluorobenzonitrile; chlorofluoro-benzoyl fluorides, such as, for example, 3-chloro-4-fluoro-benzoyl fluoride, 3-chloro-2-fluoro-benzoyl fluoride, 3-chloro-6-fluorobenzoyl fluoride, 3,5-dichloro-4-fluorobenzoyl fluoride, 3,5-dichloro-2-fluoro-benzoyl fluoride, 3-chloro-2,6-difluoro-benzoyl fluoride, 3-chloro-2,4-difluoro-benzoyl fluoride, 5-chloro-2,4-difluoro-benzoyl fluoride, 5-chloro-3,4-difluoro-benzoyl fluoride, 3,5-dichloro-2,4-difluoro-benzoyl fluoride, 3,5-dichloro-2,6-difluoro-benzoyl fluoride, 3,5-dichloro-2,4,6-trifluoro-benzoyl fluoride, chlorofluoro-trifluoromethyl-benzenes, such as, for example, 3-chloro-4-fluoro-trifluoromethyl-benzene, 3-chloro-2-fluoro-trifluoromethyl-benzene, 3-chloro-6-fluoro-trifluoromethyl-benzene, 3,5-dichloro-4-fluorotrifluoromethyl-benzene, 3,5-dichloro-2-fluoro-trifluoromethyl-benzene, 3-chloro-2,6-difluoro-trifluoromethylbenzene, 3-chloro-2,4-difluoro-trifluoromethyl-benzene, 5-chloro-2,4-difluoro-trifluoromethyl-benzene, 5-chloro-3,4-difluoro-trifluoromethyl-benzene, 3,5-dichloro-2,4-difluro-trifluoromethyl-benzene, 3,5-dichloro-2,6-difluoro-trifluoromethyl-benzene and 3,5-dichloro-2,4,6-trifluoro-trifluoromethyl-benzene; fluoro-chlorobenzenes, such as, for example, 2,3,5,6-tetrachloro-fluorobenzene and 2,3,4,6-tetrachloro-fluorobenzene; bromo-nitrofluorobenzenes, such as, for example, 5-bromo-2-fluoro-nitrobenzene; 4-fluoro-3-nitrobenzoic acid esters, such as, for example, methyl 4-fluoro-3-nitrobenzoate; nitrotrifluoromethyl-fluorobenzenes, such as, or example, 4-fluoro-3-trifluoromethyl-nitrobenzene, 2-fluoro-5-trifluoromethyl-nitrobenzene and 2,6-dinitro-4-trifluoromethyl -fluorobenzene; halogeno-benzophenones, such as, for example, 4,4'-difluoro-benzophenone; halogeno-diphenyl sulphones, such as, for example, 4,4'-difluorodiphenyl sulphone.

Substances of the type mentioned can be obtained by nucleophilic halogen-fluorine substitution in aprotic, polar solvents. In the case of tetra- or penta-chloro(-bromo)-nitrobenzenes with both ortho-positions to the nitro group occupied by chlorine(bromine), a nitrofluorine substitution also occurs to form the corresponding tetra- or penta-chloro(bromo)-fluorobenzene.

Substances of the type mentioned can also exist as a mixture in the aprotic, polar solvent, for example the mixture of isomers known from U.S. Pat. No. 3,294,629, comprising 84% of 2,5-dichloro-4-fluoro-nitrobenzene and 16% of 4,5-dichloro-2-fluoro-nitrobenzene. In the case where substances of the type mentioned are not prepared from pure precursors but instead from those of technical quality, the accompanying substances, usually chemically similar, and incompletely reacted starting materials and by-products are also obtained according to the invention.

Preferred substituted fluorobenzenes which can be obtained according to the invention are optionally substituted fluoro-nitrobenzenes of the formula

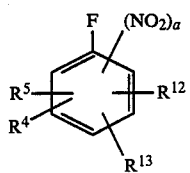

(II)

in which
a indicates the ortho- or para-position,
$R^{12}$ and $R^{13}$, independently of one another, denote hydrogen, the $NO_2$ or $CF_3$ group or halogen, where $R^{13}$ may additionally denote alkyl, and
$R^4$ and $R^5$, independently of one another, denote hydrogen or halogen.

Particularly preferred fluorobenzenes which can be obtained according to the invention are substituted fluoro-nitrobenzenes of the formula

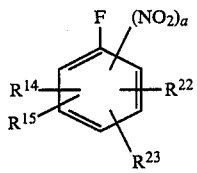

(III)

in which
a indicates the ortho- or para-position,
$R^{22}$ and $R^{23}$, independently of one another, denote the $NO_2$ or $CF_3$ group, fluorine or chlorine, where $R^{23}$ may additionally denote alkyl, and
$R^{14}$ and $R^{15}$, independently of one another, denote hydrogen, fluorine or chlorine.

In the context of the process according to the invention, aprotic, polar solvents are, for example, dimethylsulphoxide (DMSO), dimethylsulphone ($DMSO_2$), dimethylformamide (DMF), acetonitrile, tetramethylenesulphone (sulpholane; $TMSO_2$), dimethylacetamide (DMA) and hexamethyl-phosphoric acid triamide, preferably DMSO, $DMSO_2$, DMF, DMA, acetonitrile or $TMSO_2$, particularly preferably DMSO, DMF or $TMSO_2$.

Aliphatic extracting agents for the process according to the invention are straight-chain or branched, open-chain or cyclic aliphatic hydrocarbons whose boiling point is at least 30° C., such as pentane, hexane, octane, isooctane, decane, dodecane, isododecane, hexadodecane, cyclohexane, methylcyclopentane, methylcyclohexane, decalin, cyclooctane, ethyl-cyclohexane, and the aliphatic distillation cuts petroleum ethers having boiling ranges of 30°-50° C., about 40° C., 40°-60° C., 60°-70° C. and 40°-80° C., light petroleum (60°-95° C.), ligroin (80°-110° C.), soldering benzine (60°-140° C.), petroleum benzine-(100°-140° C.) and others, and also mixtures thereof with one another. In a preferred fashion, aliphatic extracting agents having a boiling point of at least 60° C. are employed, for example hexane, octane, isooctane, dodecane, isododecane, light petroleum, ligroin, soldering benzine, decalin, cyclooctane, cyclohexane, methyl-cyclohexane, ethyl-cyclohexane or petroleum benzine.

The process according to the invention is carried out at a temperature of −20 to 160° C., preferably −10° to 100° C., particularly preferably 0° to 60° C.

In principle, the process according to the invention can be carried out in batchwise extraction steps or continuously in extraction apparatuses which are known for this purpose to those skilled in the art and which are designed for extraction with relatively low-density extracting agents. 10–400 ml, preferably 40–200 ml, particularly preferably 80–140 ml, of extracting agent are used per 100 ml of the solution to be extracted in the polar, aprotic solvent per extraction step. The progress of the extraction can be followed analytically in a known fashion; the number of extraction steps necessary in a commercial procedure is a fixed quantity according to simple preliminary experiments. In the case of a continuous procedure, the subsequent work-up described below of the extract can be carried out simultaneously as long as extracting agent is always available for the first step of the process according to the invention. In such a case, the amount of extracting agent to be employed depends- only on economic considerations with respect to the recycling of this extracting agent.

If the substituted fluorobenzenes are produced in an aprotic, polar solvent or in a mixture containing such a solvent from a nucleophilic halogen-fluorine substitution reaction, the extraction according to the invention can be carried out without impairment before or after removal of the salts (for example KF/KCl), and also in the presence of any phase-transfer catalysts used.

The process according to the invention can be carried out with or without addition of water to the aprotic, polar solvents containing the substituted fluorobenzenes or mixtures containing such solvents. In the case where the solution to be extracted contains water before the extraction, a content of 0.1–15% by weight, relative to the amount of solvent, may be mentioned as an example. However, it is preferred that the process according to the invention be carried out without addition of water with substantial exclusion of moisture. The aprotic, polar solvent, or the mixture containing such a solvent, remaining after the extraction step can thus either be employed immediately in a nucleophilic substitution reaction or an uncomplicated removal of any traces of moisture is all that is required for this purpose.

The mixture containing an aprotic, polar solvent can either be a mixture of various such aprotic, polar solvents or can contain other solvents in an amount of up to 50% by weight, relative to the total weight of the aprotic, polar solvent and the other inert solvent component, such as benzene, toluene, chlorobenzene or dichlorobenzene.

The extracting agent can be removed from the substituted fluorobenzenes within the scope of the process according to the invention. This can be carried out, for example, by partly evaporating off the extracting agent until crystallization of the substituted fluorobenzene occurs. However, the extracting agent can also be selected so that its boiling point is clearly below that of the substituted fluorobenzenes. In such a case, all the extracting agent can initially be removed by disillation, after which the substituted fluorobenzenes can be obtained either by low-temperature distillation, by recrystallization or by column chromatography of the distillation residue, or by other suitable methods. Distillative removal of the extracting agent is preferred.

However, it is possible to employ the extraction solution directly for subsequent chemical reactions and to remove the extracting agent from the reaction products of the substituted fluorobenzenes. Thus, in the case of an optionally substituted fluoro-nitrobenzene, hydrogenation to form the corresponding aniline can subsequently be carried out. To this purpose, the extraction solution is employed, if appropriate after inclusion of an aqueous washing step, and is hydrogenated catalytically using H2 after addition of a suitable hydrogenation catalyst. The aliphatic extracting agent can therefore be chosen merely in view of the subsequent reaction.

The process according to the invention has the following advantages:

(1) By means of the extraction according to the invention, less stable solvents can be abandoned for the purpose of obtaining and working-up the products and temperature- and distillation-stable solvents can further be used.

(2) In the case where the aprotic, polar solvent used and the substituted fluorobenzene to be obtained have identical or similar boiling points, a mixture which can be separated by distillation can be obtained by suitable choice of the extracting agent.

(3) Compared to the aqueous work-up, described above, of solutions of substituted fluorobenzenes in aprotic, polar solvents, in which the solvent is extracted from the product by means of water, the reverse procedure according to the invention produces perfect phase separation.

(4) The process according to the invention can also carried out in the presence of the abovementioned amounts of water in the solution of the aprotic, polar solvent, although this represents the less preferred process variant. However, although the extraction time is shortened through the addition of water, the disadvantage of this less preferred process variant is, however, the necessity, mentioned above, to dry the aprotic, polar solvent again.

(5) The preferred process variant without the presence of water is very surprising in its feasibility (extraction of polar substances from polar solvents with the aid of non-polar extracting agents), since the solvent, for example DMSO, in absolute, anhydrous form has an incomparably higher capacity for aromatics than in the presence of, for example, 10% by weight of water. In addition, it permits anhydrous recovery of the aprotic, polar solvent without additional, expensive absolutization processes.

(6) In the choice of the aprotic, polar solvent, for example for a nucleophilic substitution reaction, the aspect of the boiling point of this solvent can be disregarded since, by means of the extraction according to the invention, transfer to a system which has a desired boiling point difference can be effected.

(7) Complete removal of the extracting agent from the aprotic, polar solvent presented is not particularly crucial since the extracting agent, in contrast to water, does not prevent nucleophilic substitution, and small amounts of extracting agent can thus be tolerated for use of the aprotic, polar solvent in such a nucleophilic substitution. Because of this, distillation without a column is generally sufficiently good in any subsequent removal of extracting agent from the aprotic, polar solvent which may become necessary.

(8) Through the possibility of successfully carrying out the process according to the invention with the exclusion of water, it is not only possible to isolate thermally labile compounds, but it is possible, for the first time, to also isolate hydrolyzable compounds from such solutions.

EXAMPLE 1

For extraction on a laboratory scale, a rotation perforator for Ludwig liquid-liquid extraction (German Auslegeschrift No. 2,221,554) was used. With this, 73.4 g of 3,5-dichloro-2,4-difluoro-nitrobenzene were extracted from 75 g, which had been employed in 200 ml of DMSO as solvent, in 6 hours with the aid of n-hexane as extracting agent. The temperature of the extractor was maintained at 20° C. 150 ml of n-hexane were employed per 100 ml of the DMSO3,5-dichloro-2,-difluoro-nitrobenzene mixture. The n-hexane circulated about 40 times up to the end of the extraction.

EXAMPLES 2–25

The extraction was carried out analogously to Example 1, likewise with 75 g of product in 200 ml of solvent. 100–200 ml of extracting agent, which circulated about 20–80 times in the extractor, were employed per 100 ml the solvent/substituted fluorobenzene mixture. The KF/KCl salt mixture originating from the nucleophilic chlorine-fluorine substitution reaction remained in the reaction mixture during the extraction in Example 6 and was not removed until after the extraction.

The different solvents, extracting agents and products are reproduced in the table below:

| Example | Product | Solvent | Extracting agent |
|---|---|---|---|
| 2 | 3,5-dichloro-2,4-difluoro-nitrobenzene | DMSO | cyclohexane |
| 3 | " | " | methyl-cyclohexane |
| 4 | " | " | iso-dodecane |
| 5 | " | DMF | " |
| 6 | " | " | n-hexane |
| 7 | " | CH3CN | " |
| 8 | 3,5-dichloro-2,4-difluoro-benzoyl fluoride | sulpholane | " |
| 9 | 4-fluoro-3-methyl-nitrobenzene | " | " |
| 10 | 4-fluoro-3-trifluoromethyl-nitrobenzene | " | " |
| 11 | 4-fluoro-3-chloro-benzonitrile | " | " |
| 12 | 4-fluoro-nitrobenzene | " | " |
| 13 | 3-chloro-4-fluoro-nitrobenzene | " | " |
| 14 | " | DMF | " |
| 15 | 4-fluoro-nitrobenzene | DMSO | " |
| 16 | 2-fluoro-nitrobenzene | " | " |
| 17 | " | sulpholane | " |
| 18 | 2-fluoro-5-chloro-nitrobenzene | DMSO | n-hexane |
| 19 | " | " | i-octane |
| 20 | 2,4-difluoro-5-chloro-nitrobenzene | " | n-hexane |
| 21 | 2,4-difluoro-5-chloro-nitrobenzene | DMSO | ethyl-cyclohexane |
| 22 | 2,4-difluoro-nitrobenzene | " | " |
| 23 | " | " | n-hexane |
| 24 | 4-fluoro-1,3-dinitrobenzene | " | " |
| 25 | methyl 4-fluoro-3-nitro-benzoate | " | " |

EXAMPLE 26

The batch was the same as in Example 1, but the extraction was carried out batchwise. After 20 extraction steps with the same volumes of DMSO/hexane in each case, 97% of the product had been extracted.

EXAMPLE 27

The procedure as in Example 11 was carried out, but the was replaced by a DMSO/water mixture, the product being dissolved in 180 g of DMSO and 20 g of H₂O being added.

By following the extraction analytically, it was shown that the extraction was complete after only 2 hours under otherwise identical conditions.

EXAMPLE 28

130 g of 2,3,4,5-tetrachloro-nitrobenzene (0.5 mole) were suspended in 130 g of DMSO with 75.5 g of KF (1.3 mole) and the mixture was warmed at 110° C. for 4 hours. After cooling to room temperature, the KF/KCl solid mixture was filtered off through a suction filter and washed twice with 30 ml of DMSO in each case. The DMSO solution obtained was extracted continuously with cold hexane in a 300 ml Ludwig rotation perforator for liquid-liquid extraction with specifically relatively light solvents (German Auslegeschrift No. 2,221,554 to Normag)

During this extraction, the perforator was cooled externally by water. 3,5-Dichloro-2,4-difluoro-nitrobenzene was obtained from the hexane phase in 78% yield, relative to the theoretical yield. In addition, the hexane phase contained, according to determination by gas chromatography, 10% of 2,3,4,5-tetrachloro-fluorobenzene, relative to the theoretical amount.

EXAMPLE 29

(according to U.S. Pat. No. 3,294,629; for comparison)

50 g of 2,3,4,5-tetrachloro-nitrobenzene were dissolved in 150 ml of DMSO, 30 g of KF were added, and the mixture was heated at 110° C. for 7 hours with stirring. After cooling, the mixture was poured into about 700 ml of water. During this procedure, an oily layer formed, which was taken up in about 60 ml of chloroform. The chloroform phase was washed 3 times with water, dried and concentrated under reduced pressure. Through vacuum distillation of the residue produced, 15 g of 3,5-dichloro-2,4-difluoro-nitrobenzene were obtained as a yellow oil having a boiling point of 71°-75.5° C./2 mm Hg. This corresponds to 34% of the theoretical yield.

We claim:

1. In a process for obtaining substituted fluorobenzenes from aprotic, polar solvents or mixtures containing such solvents, the improvement wherein the substituted fluorobenzenes are extracted from the solvents/solvent mixtures with aliphatic hydrocarbon extracting agents, and the extracting agents are then separated from the substituted fluorobenzenes.

2. Process according to claim 1, wherein the substituted fluorobenzenes are those of the general formula

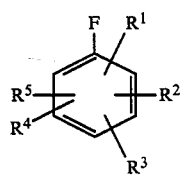

(I)

in which
$R^1$ represents an NO₂, CN, COF or CF₃ group which is in the ortho- or para-position to the fluorine and, in the case where at least three of the radicals $R^2$ to $R^5$ represent chlorine or bromine, of which one is in the ortho-position to the fluorine, the second may also be chlorine or bromine in the ortho-position, $R^2$ denotes hydrogen, halogen or an NO₂, CN, COF, CF₃, COOR⁶, COR⁷, SP₂R⁷, SO₂—N(R⁶)₂ or CO—N(R⁶)₂ group, in which
  $R^6$ denotes alkyl or phenyl, and
  $R^7$ denotes alkyl, phenyl or substituted phenyl,
$R^3$ denotes hydrogen, halogen, alkyl or an NO₂ group, and
$R^4$ and $R^5$, independently of one another, denote hydrogen or halogen.

3. Process according to claim 2, wherein the substituted fluorobenzenes are fluoro-nitrobenzenes substituted fluro-nitrobenzenes of the formula

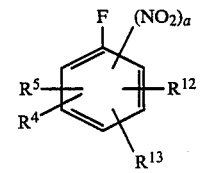

(II)

in which
a indicates the ortho- or para-position,
$R^{12}$ and $R^{13}$, independently of one of another, denote the NO₂ or CF₃ group, halogen,
where $R^{13}$ may additionally denote alkyl, and
$R^4$ and $R^5$, independently of one another, denote hydrogen or halogen.

4. Process according to claim 3, wherein the substituted fluorbenzenes are substituted fluoro-nitrobenzenes of the formula

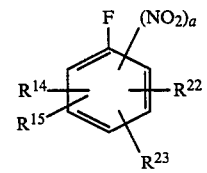

(III)

in which
a indicates the ortho- or para-position,
$R^{22}$ and $R^{23}$, independently of one another, denote the NO₂ or CF₃ group, fluorine or chlorine, where $R^{23}$ may additionally denote alkyl, and
$R^{14}$ and $R^{15}$, independently of one another, denote hydrogen, fluorine or chlorine.

5. Process according to claim 1, wherein the aprotic, polar solvent is dimethylsulphoxide (DMSO), dimethylsulphone (DMSO₂), tetramethylenesulphone (TMSO₂, sulpholane), dimethylformamide (DMF), dimethylacetamide (DMA) or acetonitrile.

6. Process according to claim 5, wherein the aprotic, polar solvent is DMSO, DMF or TMSO₂.

7. Process according to claim 1, wherein the extracting agent is hexane, octane, isooctane, dodecane, isodecane, light petroleum, ligroin, soldering benzine, decalin, cyclooctane, cyclohexane, methylcyclohexane, ethyl-cyclohexane or petroleum benzine.

8. Process according to claim 1, wherein the extraction is carried out at a temperature from −20° to 160° C.

9. Process according to claim 8, wherein the extraction is carried out at a temperature from −10° to 100° C.

10. Process according to claim 9, wherein the extraction is carried out at a temperature form 0° to 60° C.

11. Process according to claim 1, wherein the extraction is carried out without addition of water.

12. Process according to claim 1, wherein the removal of the extracting agent from the substituted fluorobenzenes is carried out by distillation.

13. Process according to claim 1, wherein 10–400 ml of extracting agent are used per 100 ml of the solution to be extracted per extraction step.

14. Process according to claim 13, wherein 40–200 ml of extracting agent are used per 100 ml of the solution to be extracted per extraction step.

15. Process according to claim 14, wherein 80–140 ml of extracting agent are used per 100 ml of the solution to be extracted per extraction step.

16. Process according to claim 1, characterized in that the extraction is carried out continuously.

* * * * *

UNITED STATES PATENT AND TRADEMARK OFFICE
CERTIFICATE OF CORRECTION

PATENT NO. : 4,868,347

DATED : September 19, 1989

INVENTOR(S) : Blank et al.

It is certified that error appears in the above-identified patent and that said Letters Patent is hereby corrected as shown below:

| | |
|---|---|
| Title Page | ABSTRACT: Lines 5-6 delete " seaprating " and substitute -- separating -- |
| Col. 10, line 4 | Delete " $SP_2R^7$ " and substitute -- $SO_2R^7$ -- |
| Col. 10, lines 13-14 | Delete " fluoro-nitrobenzenes substituted fluro-nitrobenzenes " |
| Col. 10, line 26 | After " denote " add -- hydrogen, -- |
| Col. 10, line 27 | Delete " , " and substitute -- or -- |
| Col. 12, lines 10-11 | Delete " characterized in that " and substitute -- wherein -- |

Signed and Sealed this

Fourth Day of December, 1990

Attest:

HARRY F. MANBECK, JR.

Attesting Officer

Commissioner of Patents and Trademarks